United States Patent [19]

Köhler

[11] Patent Number: 5,280,784
[45] Date of Patent: Jan. 25, 1994

[54] DEVICE IN PARTICULAR AND INHALATING DEVICE FOR TREATING THE LUNG AND THE RESPIRATORY TRACTS

[75] Inventor: Dieter Köhler, Schmallenberg-Winkhausen, Fed. Rep. of Germany

[73] Assignee: Paul Ritzau Pari-Werk GmbH, Starnberg, Fed. Rep. of Germany

[21] Appl. No.: 972,096

[22] Filed: Nov. 5, 1992

Related U.S. Application Data

[63] Continuation of Ser. No. 761,432, Sep. 18, 1991, abandoned.

[30] Foreign Application Priority Data

Sep. 19, 1990 [DE] Fed. Rep. of Germany ....... 4029680

[51] Int. Cl.⁵ ..................... A61M 11/00; A61M 15/00
[52] U.S. Cl. .................. 128/200.14; 128/200.16; 128/200.21; 128/204.21; 128/205.24; 128/203.12
[58] Field of Search ............ 128/200.14, 200.21, 128/200.22, 200.16, 204.27, 203.12, 203.14, 204.21, 204.18, 204.25, 205.12, 205.24, 207.16; 251/336, 337; 261/DIG. 65, DIG. 48

[56] References Cited

U.S. PATENT DOCUMENTS

| 1,988,979 | 1/1935 | Campbell | 128/200.23 |
|---|---|---|---|
| 2,691,548 | 10/1954 | Feucht et al. | 128/200.23 |
| 2,774,346 | 12/1956 | Halliburton | 128/200.11 X |
| 2,918,917 | 12/1959 | Emerson | 128/205.25 |
| 3,537,448 | 11/1970 | Liston | 128/200.21 |
| 3,580,249 | 5/1971 | Takaoka | 128/200.14 |
| 3,702,114 | 11/1972 | Zacarian | 128/200.23 |
| 3,769,973 | 11/1973 | Esbenshade | 128/200.14 |
| 3,915,164 | 10/1975 | Bird | 128/200.14 |
| 4,054,134 | 10/1977 | Kritzer | 128/204.18 |
| 4,259,951 | 4/1981 | Chernack | 128/200.14 |
| 4,328,796 | 5/1982 | Hakkinen | 128/200.14 |
| 4,396,015 | 8/1983 | Johnson | 128/200.14 |
| 4,606,340 | 8/1986 | Ansite | 128/205.24 |
| 4,677,975 | 7/1987 | Edgar et al. | 128/200.14 |
| 4,747,402 | 5/1988 | Reese et al. | 128/204.21 |
| 4,747,403 | 5/1988 | Gluck et al. | 128/205.24 |
| 4,793,339 | 12/1988 | Matsumoto et al. | 128/200.16 |
| 4,821,709 | 4/1989 | Jensen | 128/204.21 |
| 4,832,012 | 5/1989 | Raabe et al. | 128/200.21 |
| 4,986,269 | 1/1991 | Hakkinen | 128/200.21 X |

FOREIGN PATENT DOCUMENTS

| 2926659 | 1/1981 | Fed. Rep. of Germany | 128/203.12 |
|---|---|---|---|
| 6507511 | 12/1965 | Netherlands | 128/200.22 |

*Primary Examiner*—Theatrice Brown
*Assistant Examiner*—Sebastiano Passaniti
*Attorney, Agent, or Firm*—Brooks Haidt Haffner & Delahunty

[57] ABSTRACT

An inhaling device for treating the lungs and respiratory tracts of humans or animals has a pressurized gas source, an atomizer connected to the gas source in a pressure conveying manner, a mouthpiece connected to the atomizer, and a spent gas flue. A valve for periodically interrupting the flow of exhaled air is provided in the region of the spent gas flue. The valve is activated by a control unit.

8 Claims, 1 Drawing Sheet

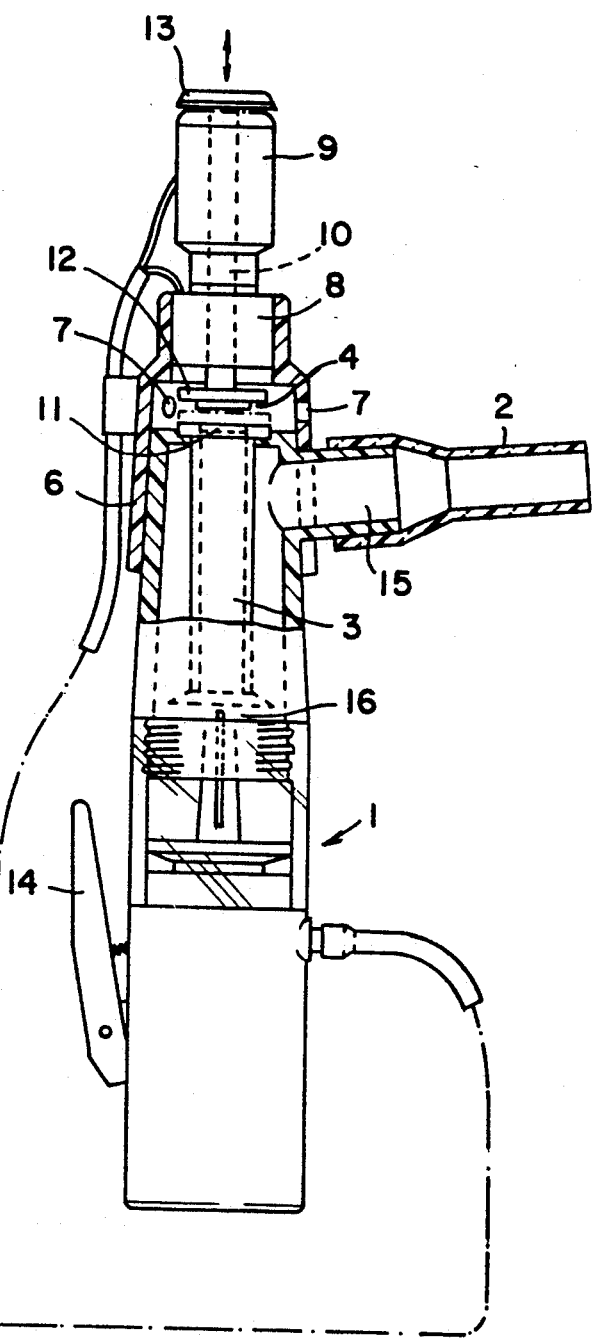

DEVICE IN PARTICULAR AND INHALATING DEVICE FOR TREATING THE LUNG AND THE RESPIRATORY TRACTS

This application is a continuation of application Ser. No. 07/761,432, filed Sept. 18, 1991 now abandoned.

BACKGROUND OF THE INVENTION

1. Field of the Invention

The invention relates to a device, in particular an inhalating device for treating the lung and the respiratory tracts of humans or animals, comprising a pressurized gas source, an atomizer connected with this in a pressure conveying manner, and a mouthpiece connected with the atomizer and a spent air flue.

2. Description of the Prior Art

A device of this type is already known from EP 0 311 770. This document describes a breathing therapy device for persons suffering from asthma or spastic bronchitis and has a housing comprising a mouthpiece, an air intake duct and an air discharge duct. The air intake duct includes a connection for an inhalating substance applicator in which a medication can be atomized. For the peak flow measurement, a standpipe leading to atmosphere comprising a floated element, the rise of which indicates the volumetric flow of the exhaled air, is connected with the air discharge duct. A valve arrangement closes the air discharge duct during inhalation and the air intake duct during exhalation.

With this kind of inhalating device, however, medications can only be administered to the respiratory tracts in a finely atomized manner or in the form of vapor without the normal flow of inhaled or exhaled air being interrupted.

Problems arise with the mucus expectoration, in particular in patients with chronic obstructive bronchitis and increased collapsibility of the respiratory tracts. However, in forced breathing maneuver, such as coughing, for example, in which mucus is to be removed from the respiratory tracts, the mucus transport is stopped as a result of the closure of a part of the bronchi.

A device for inducing artificial coughing is also known from DE 31 19 814. A treatment is conducted with such a device in which a sudden pressure drop is induced in the respiratory tracts of the patient to generate a flow of exhaled air with the strength of a strong cough. Such treatment leads to reduction in the collapse of the bronchi but on the other hand includes the disadvantage of reducing the rate of flow of breath with the resulting weaker transport force for the mucus.

It is therefore an object of the invention to provide a device, in particular an inhaling device of the type initially mentioned with which the transport of mucus out of the respiratory tracts of the patients can be improved.

SUMMARY OF THE INVENTION

This object is solved in accordance with the invention in that a valve is arranged in the region of the spent air flue for periodically interrupting the flow of exhaled air, the valve being operated by means of a control unit. With such an inhaling device, the patient can actively breathe out against the quickly closing and quickly opening valve. The frequency and the opening time of the valve are separately adjustable in the control unit. Preferably, the opening time is set such that the pressure in the bronchial system due to the collapse ensuing in the respiratory tracts is only just preventing from subsiding. Additionally, the required high rate of the flow of breath for the transport of the mucus is maintained. A periodic shaking up of the phlegm also occurs. The frequency range for the closing and opening of the valve is set by the patient according to subjective criteria, an interruption frequency of approximately 10 Hz having shown itself to be advantageous. In tests with the inventive device compared to normal coughs, an increase in the quantity of sputum of about +12.2% was determined. The peak flow increased somewhat to approximately 7±3%.

In accordance with a preferred embodiment, the valve is arranged with its actuating element in a housing on the atomizer above the spent air flue which exits out of the atomizer. This has the advantage that the valve can be arranged on the atomizer to be removable from the outside and that the device can also be used exclusively as an inhalating device.

In accordance with a further embodiment of the invention, openings for the discharge of air are provided in the housing of the valve. A further advantageous embodiment of the invention is that the spent air flue is simultaneously an inlet air flue. This renders valves for a separate inlet and spent air flues unnecessary.

It is further suggested in accordance with the invention that the actuating element of the valve consists of at least one electromagnet. With such magnets, the valve head can be lifted off the valve seat against the force of gravity if an electric impulse emitted by the control unit actuates these electromagnets.

A further advantageous embodiment of the invention provides for that the actuating element has a first electromagnet for opening the valve and a second electromagnet for closing the valve. This implies that a reliable, quick and precise opening and closing of the valve can be carried out without delays arising on account of the unnecessarily large acceleration times of the moved valve parts.

In a particularly advantageous embodiment of the invention, the actuating element has two coaxially opposed electromagnets within which a valve stem is coaxially guided. This valve stem projects above the electromagnets, a part consisting of ferromagnetic material is arranged at its end which is distal from the valve seat while the end facing the valve seat has a ferromagnetic part with a valve head. This valve head can be placed in a sealing manner on the valve seat arranged on the spent air flue. The ferromagnetic parts at the ends of the valve stem advantageously also serve as a stop for the valve stem against the electromagnets.

A further useful embodiment of the invention provides that the actuating element consists of an electromagnet connected with the control unit and a spring element acting against acting against the electromagnet. In this manner, the valve can be opened against the spring force of the spring element through actuation of the electromagnet. When the electromagnet is switched off, the valve is closed by the spring element.

It is also suggested in accordance with the invention that the control unit is connected to an interval lever of the atomizer which is to be actuated during inhalation. Thus, one can achieve that an atomization takes place by actuating the interval lever during inhalation, and in not actuating the interval lever when exhaling, the spent air flue is periodically opened and closed by the valve so that the exhaled air flow is interrupted.

It is also possible to pneumatically actuate the valve. The impulse would then also come from the control unit.

BRIEF DESCRIPTION OF THE DRAWING

In the drawings:

FIG. 1 is a schematic, elevation view, partly in cross-section, of an embodiment of the invention; and FIG. 2 is a fragmentary, elevation view, partly in cross-section of a modification of the embodiment shown in FIG. 1.

DESCRIPTION OF THE PREFERRED EMBODIMENTS

FIG. 1 shows an atomizer 1 which is connected with a control unit 5 via a pressure line. This atomizer has an atomizing region 16 in which liquid medication is finely atomized. An inlet or spent air flue 3 is also arranged in the atomizer and has an opening into the atomizing region 16. An inhaling and exhaling conduit 15 with a mouthpiece 2 placed thereon enters into the atomizing region 16. The atomizer can be actuated with an interval lever 14 mounted onto the atomizer.

A valve 4 arranged in a housing 6 is releasably connected to the atomizer by insertion onto the top of the atomizer. The valve 4 with its valve head of ferromagnetic material 12 closes onto a valve seat 11 which is arranged at the outlet of the spent air flue 3. The exhaled air flow can escape in the open state of the valve through the air outlet opening 7 which is arranged in the valve housing 6.

Electromagnets 8, 9 are respectively provided for opening and closing the valve. These electromagnets 8, 9 are arranged coaxially above one another, a valve stem 10 which projects above the electromagnets 8, 9 being guided in these. a part 13 consisting of ferromagnetic material which is attracted by the upper electromagnet 9 to close the valve is arranged at the end of the valve stem 10 distal from the valve seat. The ferromagnetic material 12 which is arranged at the end of the valve stem 10 facing the valve seat 11 is attracted by the lower electromagnet 8 to open the valve 4.

Both electromagnets 8, 9 are actuated by the control unit 5, and during the inhalation phase, the valve 4 is open and the lower electromagnet 8 attracts the ferromagnetic material 12 comprising the valve head 11, while the upper electromagnet 9 is not actuated. In the exhaling step when the interval lever 14 is not actuated, the electromagnets 8, 9 are alternatively actuated by the control unit 5 with a certain predetermined frequency so that the exhaling flow is interrupted corresponding to this frequency. The frequency and the duration of actuation of the electromagnets are separately adjustable in the control unit 5.

On account of the sudden build-up and release of pressure in the respiratory tracts of the patient during closing and opening of the valve 4, against which the patient actively breathes, the phlegm in the respiratory tracts of the patient can be periodically shaken up. The opening time of the valve 4 is set such that the pressure in the bronchial system, due to the resulting collapse of the bronchial system during a sudden pressure fall, is only just prevented from subsiding by opening the valve 4. Simultaneously, the high rate of exhaled air flow is maintained for the transport of the mucus.

FIG. 2 shows a modification of the embodiment shown in FIG. 1 in which the electromagnet 9 is replaced by a spring element 17 to close the valve 4.

This new equipment which can be used in connection with inhaling devices and respiration apparatus is a substantial contribution to physical therapy for patients with obstructive lung ailments with mucus retention.

I claim:

1. An inhaling device for treating the lung and the respiratory tracts of humans or animals, comprising a pressurized gas source, an atomizer connected with said gas source in a pressure conveying manner, a mouthpiece connected with the atomizer and a spent air flue wherein a valve for periodically interrupting the flow of exhaled air is arranged in the region of the spent air flue and further comprising valve actuating means comprising an electromagnet connected to a control unit for energizing said electromagnet and connected to said valve for operating said valve and a spring element connected to said valve and acting against said electromagnet.

2. In an inhaling and exhaling device for treating the lung and respiratory tracts of humans and animals, said device comprising:
   a housing having a gas chamber therewithin and an opening outside said chamber extending to the atmosphere;
   an atomizer connected to said chamber for supplying gas and atomized medication to said chamber;
   a source of gas under pressure above atmospheric pressure connected to said atomizer for supplying gas to said atomizer; and
   mouthpiece means on said housing and having a passageway leading to said chamber whereby inhalation gas passes along a path extending from said chamber and out of said mouthpiece means and exhalation gas passes along a path extending from said mouthpiece means toward said chamber;
wherein the improvement comprises:
   valve means periodically operable from externally of said housing and in said path extending from said mouthpiece means toward said chamber, said valve means being alternately operable from an open position which permits gas to flow along said path from said mouthpiece means toward said chamber and to a closed position which prevents the flow of gas along said path from said mouthpiece means toward said chamber and said valve means comprises a spent air flue extending from said chamber to adjacent said opening, a valve for opening and closing said spent air flue and valve actuating means connected to said valve and mounted on said housing; and
   a control unit connected to said valve means for periodically operating said valve means from its open position to its closed position, and vice versa, independently of the gas pressure at said mouthpiece means
whereby the flow of gas through said mouthpiece means is periodically interruptible while the human or animal is exhaling.

3. A device as set forth in claim 2 wherein when said valve is open, air is permitted to flow into said chamber from said opening.

4. A device as set forth in claim 2 wherein said valve actuating means comprises at least one electromagnet.

5. A device as set forth in claim 4 wherein said valve actuating means comprises a first electromagnet for closing said valve and a second electromagnet for opening said valve.

6. A device as set forth in claim 5 wherein said valve has a valve stem, a first ferromagnetic part at one end of said stem and adjacent and engageable with an end of said spent air flue and a second ferromagnetic part at an opposite end of said stem, said first electromagnet being adjacent said second ferromagnetic part for closing said valve with energization of said first electromagnet and said second electromagnetic being adjacent said first ferromagnetic part for opening said valve with energization of said second electromagnet.

7. A device as set forth in claim 2 wherein the period at which said control unit moves said valve means between its open position and its closed position is up to about 10 Hz.

8. A device as set forth in claim 2 wherein said atomizer has a manually operable lever for actuation of said atomizer.

* * * * *